United States Patent [19]
Hildebrand

[11] Patent Number: 5,530,368
[45] Date of Patent: Jun. 25, 1996

[54] CAPACITIVE SENSOR FOR DETECTING FLUCTUATIONS IN THE MASS AND/OR DIAMETER OF ELONGATED TEXTILE TEST MATERIAL

[75] Inventor: Niklaus Hildebrand, Wald, Switzerland

[73] Assignee: Zellweger Luwa AG, Switzerland

[21] Appl. No.: 127,490

[22] Filed: Sep. 28, 1993

[30] Foreign Application Priority Data

Oct. 1, 1992 [CH] Switzerland ............... 03066/92

[51] Int. Cl.⁶ ............... G01R 27/26; H01G 5/00
[52] U.S. Cl. ............ 324/662; 361/278; 324/671
[58] Field of Search .................. 324/687, 688, 324/690, 671, 662; 361/278; 73/160

[56] References Cited

U.S. PATENT DOCUMENTS

| | | | |
|---|---|---|---|
| 3,009,101 | 11/1961 | Locher | 324/690 |
| 3,039,051 | 6/1962 | Locher | 324/671 |
| 3,341,774 | 9/1967 | Dyben | 324/671 |
| 3,377,852 | 4/1968 | Leistra | 361/278 |
| 3,471,780 | 10/1969 | Beddows | 324/671 |
| 3,679,972 | 7/1972 | Michelson | 324/671 |
| 3,754,172 | 8/1973 | Hoffman | 361/278 |
| 4,140,898 | 2/1979 | Gasser et al. | 73/160 |
| 4,208,625 | 6/1980 | Piso | 324/671 |
| 4,311,958 | 1/1982 | Aeppli | 73/160 |
| 4,947,131 | 8/1990 | Mayer et al. | 324/671 |
| 4,952,882 | 8/1990 | Mayer et al. | 324/690 |
| 5,121,068 | 6/1992 | Baker | 324/690 |

FOREIGN PATENT DOCUMENTS

0165754  10/1982  Japan ................... 324/689

OTHER PUBLICATIONS

"The Mini Uster Portable Uniformity Testing Instrument", Uster News Bulletin No. 28, Chapter 1.6, Jul. 1980.

*Primary Examiner*—Maura K. Regan
*Attorney, Agent, or Firm*—Burns, Doane, Swecker & Mathis

[57] ABSTRACT

A capacitive sensor has a pair of plate-shaped electrodes (4) spaced apart from one another and defining a measurement slot (3) therebetween. Guides (5) mask out edge zones of the measurement slot (3) and reduce its width. These guides (5) are formed as the two legs of an elongated U-shaped guiding part (7) which can be inserted into the measurement slot (3) and can be fixed in the latter.

7 Claims, 1 Drawing Sheet

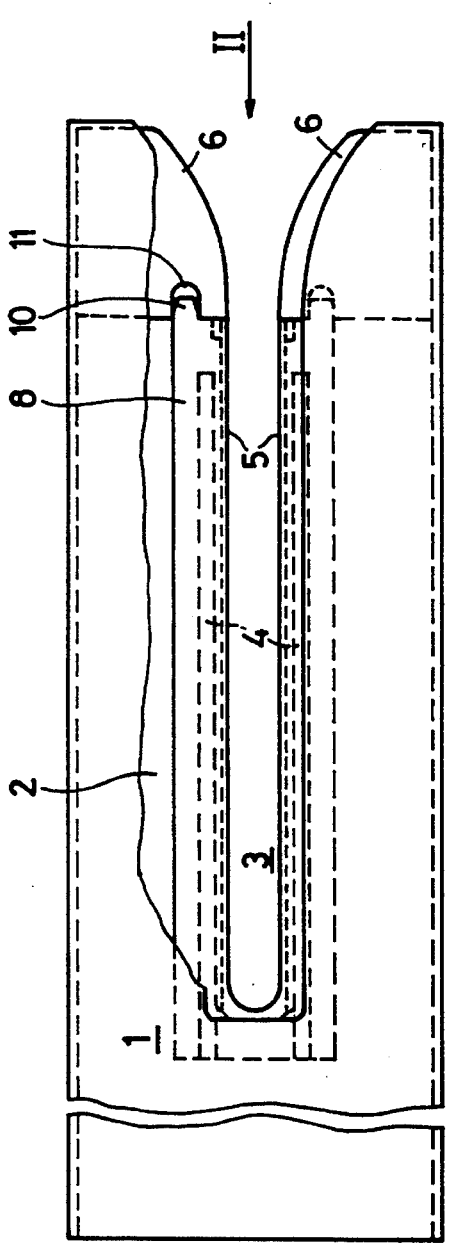
FIG. 1
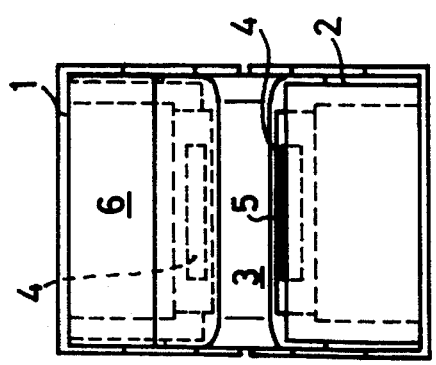
FIG. 2
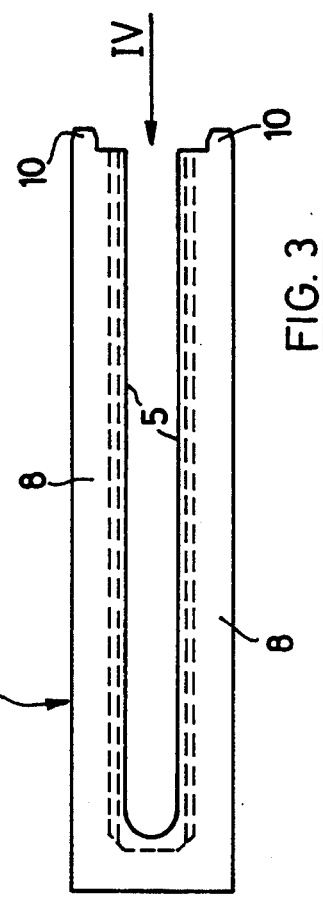
FIG. 3
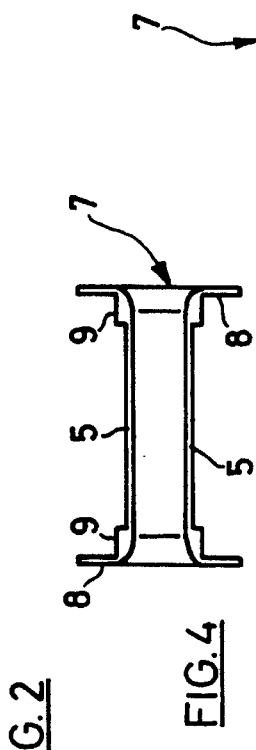
FIG. 4
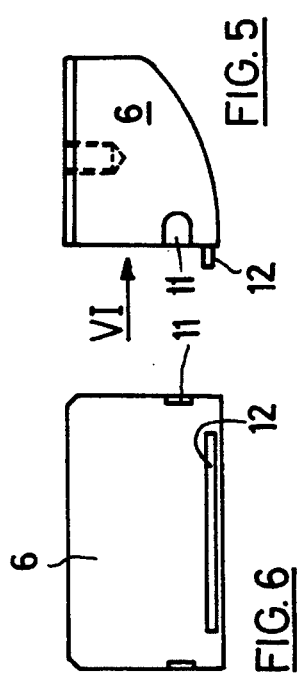
FIG. 5
FIG. 6

CAPACITIVE SENSOR FOR DETECTING FLUCTUATIONS IN THE MASS AND/OR DIAMETER OF ELONGATED TEXTILE TEST MATERIAL

FIELD OF THE INVENTION

The present invention relates to capacitive sensors for detecting fluctuations in the mass and/or diameter of elongated textile test material such, for example, as cotton slivers. These sensors are of the type in which plate-shaped electrodes delimit a measurement slot provided for the passage of the test material.

BACKGROUND

Such sensors have a so-called shape effect and a so-called position effect. Shape effect means that test material not of exactly cylindrical cross-section generates signals of different strength depending on its transverse position in the measurement slot. Position effect means that material of arbitrary cross-section generates signals of different strength depending on its position between the measurement electrodes. In optical sensors, where the shape effect is particularly strong, an attempt is made to overcome the latter by scanning the test material using two mutually crossed light bundles. In capacitive sensors, in which the shape effect is substantially weaker but the position effect substantially stronger than in the optical sensors, attempts have been made to date to equalize possible deviations of the test material from the cylindrical cross-section by rotating the test material about its axis, and to achieve accurate positioning by complicated guides for the test material outside the measurement zone. With increasing demands on measurement accuracy, these methods tend to be increasingly unsatisfactory, and they also place high demands on the take-off means and transport means for the test material.

SUMMARY OF THE INVENTION

An aim of the present invention is to provide improved capacitive sensors in which the shape effect and the position effect are excluded or at least reduced to a negligible magnitude of distinctly less than 10%.

It is a feature of this invention that mechanical means are provided for masking out the edge zones of the measurement slot. In accordance with a preferred embodiment, the mechanical means are formed by guides which reduce the width of the measurement slot.

By means of these guides, the test material is guided at a defined distance from the electrodes and can thus no longer reach into the edge zones of the measurement slot. The portions of the test material which previously reached too close to the electrodes are thereby guided at a greater distance from the electrodes. It was precisely these portions of the test material (i.e., the portions which previously reached into the vicinity of the electrodes) which have been overrated during the testing by up to 20%. As a result of preventing the test material from approaching close to the electrodes, measuring errors caused by the shape effect and/or the position effect are significantly reduced.

BRIEF DESCRIPTION OF THE DRAWINGS

The invention will be explained in more detail below with the aid of an exemplary embodiment illustrated in the drawings, wherein FIG. 1 shows a plan view of a measuring probe having a capacitive sensor for measuring the non-uniformity of yarns or slivers;

FIG. 2 shows a view in the direction of the arrow II of FIG. 1;

FIG. 3 shows a first detail of FIG. 1;

FIG. 4 shows a view in the direction of the arrow IV of FIG. 3;

FIG. 5 shows a second detail of FIG. 1; and

FIG. 6 shows a view in the direction of the arrow VI of FIG. 5.

DETAILED DESCRIPTION OF THE PREFERRED EMBODIMENT

FIG. 1 shows a plan view of a measuring probe of a tester for running lengths of fiber slivers. An example of such a tester is the MINI USTER test unit offered by Zellweger Uster AG for measuring the non-uniformity of yarns or slivers directly on the respective machine. (MINI USTER and USTER are registered trademarks of Zellweger Uster AG.)

The measuring probe 1 includes an elongated housing 1 (partially broken away in FIG. 1) which contains a retaining block 2 for two plate-shaped metal electrodes 4 arranged on both sides of a measurement slot 3. Guides 5 cover the electrodes 4 with respect to the measurement slot 3 and are made of non-conductive material. Two jaws 6 adjoin the electrodes 4 and form a funnel-shaped extension for facilitating the lateral insertion of the test material into the measurement slot 3.

FIG. 2 shows a view into the base of the measurement slot 3, with the lower jaw 6 in FIG. 1 being omitted. FIGS. 3 and 4 show two views of the component supporting the guides 5, and FIGS. 5 and 6 show two views of the lower jaw 6 in FIG. 1.

The electrodes 4 form in a known way a capacitive sensor for measuring fluctuations in the mass and/or diameter of test material such as yarns and slivers running through the measurement slot 3. The measurement probes for the MINI USTER can be obtained in slot widths between six and twelve millimeters. The measurement probe represented in the drawings is one for slivers and has a slot width of 12 mm.

The MINI USTER test equipment is disclosed, for example, in the USTER News Bulletin No. 28 of Jul. 1980, chapter 1.6 "The MINI USTER Portable Uniformity Testing Instrument", the disclosure of which is incorporated herein by reference. Hence, it will not be described here in detail but only to the extent required for understanding the invention. Moreover, it is expressly pointed out that the invention is not, of course, limited to the MINI USTER but can be used in all capacitive sensors for measuring the non-uniformity of textile test material. Such sensors are used, for example, in the known USTER TESTER uniformity testers and in the electronic USTER AUTOMATIC, USTER POLYMATIC and USTER POLYGUARD yarn clearers.

The guides 5, which prevent the test material from being able to reach too near to the electrodes 4, serve to avoid the shape effect and the position effect. The first of these consists in that non-cylindrical test material generates signals of different strength depending on its position in the measurement slot 3. The position effect means that test material of whatever cross-section likewise generates signals of different strength depending on its position between the electrodes 4. If the position-dependent sensitivity of a capacitive sensor is plotted as a change in sensitivity in percent as a function of the measurement slot width, the result is a curve in the shape of a bath tub, a U-shape in which tapers appear at the margins. This curve of the signal generated shows that test material guided in the middle of the measurement slot 3 will be rated differently from test material at the edges of the slot. Test material located closer to an electrode than a distance equal to 10% of the slot width may be overrated up to 20%.

If the portion of the space between the electrodes or plates 4 which can be occupied by the textile strand is reduced to the middle 80% of the width by means of the guides 5, with an edge region of 10% on each side being masked out, the maximum change in sensitivity is distinctly less than 10%, and less than 4% in the case of a masked-out edge region on each margin of approximately 15% of the slot width. Thus, in the case of the measurement probe represented in the drawings, which has a slot width of 12 mm, a distance of 2 mm between each of the guides 5 and its adjacent electrode 4 has proved to be optimum.

The guides 5 preferably form the two limbs of a U-shaped guiding part 7 which can be inserted into the measurement slot 3 and fixed in the latter. The illustrated guiding part 7 is formed from an elongated band or ribbon of groove-like transverse cross section. The band is folded in the shape of a U in a molding operating that provides the U-shaped guiding part 7. The cross sectional shape of the band provides a base part which forms the guides 5 and lateral webs 8 projecting from such base part to form collars at the sides of the unit. The lateral webs serve to fix the guiding part 7 against motion relative to the probe body in the direction of movement of the test material through the measurement slot 3. In FIG. 1, this is the direction perpendicular to the plane of the drawing. As can be gathered from FIG. 2 in particular, the lateral webs 8 of the guiding part 7 embrace the retaining block 2 for the electrodes 4 to accomplish this purpose.

A step 9 is provided in the transition regions between the base part of the guide 5 and each of the lateral webs 8 at the margins of the ribbon that is used to form the part 7. These steps 9 have the effect of distancing or spacing the guides 5 from the electrodes 4. Of course, the guides 5 can also be built directly onto the electrodes 4.

At their free ends, each of the lateral webs 8 ends in a fixing nose 10 which engages in a corresponding groove 11 formed in the adjacent jaw 6. As a further fixing means for the guiding part 7, each of the jaws has a projecting web 12 which acts on the rear of the base part of the sectional ribbon which forms the guide 5. Hence, the guiding part 7 is firmly clamped in the region of its free ends by the fixing noses 10 engaging in the grooves 11 and by the webs 12 which fix the position of the guides 5.

The material used for the guiding part 7 is a suitable plastic which may, in particular, be electrically non-conductive and should have a dielectric constant as small as possible. Moreover, the guiding part 7 must be mechanically and chemically stable. No chemical reactions should be allowed to take place between the test material and the guides 5. In practical trials, polyacetal (polyoxymethylene) resins have proved to be particularly suitable. Apart from its good properties, this material is also very low-priced and is easy to process.

What is claimed is:

1. A capacitive sensor having a gap through which a running length of elongated textile test material is drawn, said sensor comprising a capacitor made up of first and second electrodes on opposite sides of said gap, means for confining the textile material in a predetermined area in the gap that is spaced from the electrodes to reduce a position effect associated with the electrodes, said means including a first guide between said first electrode and said gap for assuring that all portions of said running length of textile test material will be spaced at least a predetermined distance away from said first electrode and a second guide between said second electrode and said gap for assuring that all portions of said running length of textile test material will be spaced at least a predetermined distance away from said second electrode, said first guide being spaced from said first electrode along at least a portion of the length of the first guide so that a space exists between the first guide and the first electrode, and said second guide being spaced from said second electrode along at least a portion of the length of the second guide so that the second guide is spaced from the second electrode.

2. A sensor according to claim 1, wherein the sides of said guides which face one another are spaced apart a distance no greater than about 80% of the distance between said electrodes.

3. A sensor according to claim 1, wherein said first and second guides are mounted on a retaining block.

4. Sensor according to claim 1, wherein said first and second guides are made of non-conductive material.

5. Sensor according to claim 4, wherein said first and second guides are made of a plastic material having a low dielectric constant.

6. A capacitive sensor for detecting fluctuations in the mass and/or diameter of running lengths of elongated textile test material comprising a retaining block having an open-ended slot therein through which the test material may be passed; a first capacitor plate on said retaining block and extending along one side of said slot; a second capacitor plate on said block generally parallel to said first plate and extending along an opposite side of said slot in spaced relation to said first plate; guide means of nonconducting plastic material having a low dielectric constant for confining the textile test material in a predetermined area of the slot to reduce a position effect associated with the first and second capacitor plates, the guide means being disposed in said slot and having first and second guide portions for preventing close approach of the test material to said capacitor plates; and jaw members attachable to said retaining block near the open end of said slot to facilitate lateral insertion of said test material into said slot, said jaw members fixing said guide means in place in said slot upon attachment of said jaw members to said block.

7. A sensor according to claim 6, wherein said first guide portion has an inner surface facing away from said first capacitor plate toward the middle of said slot, said inner surface of said first guide portion being spaced from said first plate a distance which is about 10 to about 30 percent of the distance between said first and second capacitor plates; and wherein said second guide portion has an inner surface facing away from said second capacitor plate toward the middle of said slot, said inner surface of said second guide portion being spaced from said second plate a distance which is about 10 to about 30 percent of the distance between said first and second capacitor plates.

* * * * *